United States Patent
Yang et al.

(10) Patent No.: US 10,343,151 B2
(45) Date of Patent: *Jul. 9, 2019

(54) PROCESS FOR PRODUCING A MOLECULAR SIEVE HAVING THE SFE STRUCTURE, MOLECULAR SIEVE HAVING THE SFE STRUCTURE AND USE THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Zhendong Wang, Shanghai (CN); Hongmin Sun, Shanghai (CN); Bin Zhang, Shanghai (CN); Yi Luo, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (*) Notice: Subject to any disclaimer, the term of this patent is extended or adjusted under 35 U.S.C. 154(b) by 188 days.

This patent is subject to a terminal disclaimer.

(21) Appl. No.: 15/347,142

(22) Filed: Nov. 9, 2016

(65) Prior Publication Data

US 2017/0128924 A1 May 11, 2017

(30) Foreign Application Priority Data

Nov. 9, 2015 (CN) .......................... 2015 1 0753821

(51) Int. Cl.
*C01B 39/48* (2006.01)
*C01B 39/02* (2006.01)
(Continued)

(52) U.S. Cl.
CPC ............... *B01J 29/86* (2013.01); *B01J 29/89* (2013.01); *C01B 39/00* (2013.01); *C01B 39/02* (2013.01);
(Continued)

(58) Field of Classification Search
CPC ......... C01B 39/48; C01B 39/00; C01B 39/02; C01B 39/12; B01J 29/70; B01J 29/86; B01J 29/89; C07C 2/66; C07C 2529/86
See application file for complete search history.

(56) References Cited

U.S. PATENT DOCUMENTS 2,882,243 A 4/1959 Milton
2,882,244 A 4/1959 Milton
(Continued)

FOREIGN PATENT DOCUMENTS

JP 4990145 B2 8/2012

OTHER PUBLICATIONS

Jose G. Nery et al. On the synthesis of SSZ-48, SSZ-43 and their variations, Microporous and Mesoporous Materials, Jan. 3, 2002, pp. 19-28, vol. 52, Issue 1, Elsevier.
(Continued)

*Primary Examiner* — David M Brunsman
(74) *Attorney, Agent, or Firm* — Novick, Kim & Lee, PLLC

(57) ABSTRACT

The present invention relates to a molecular sieve having the SFE structure, a process for producing same and use thereof. The process includes a step of crystallizing a mixture comprising a first oxide source, a second oxide source, an organic template and water to obtain a molecular sieve having the SFE structure, wherein the organic template is preferably 4-dimethylamino pyridine. As compared with the prior art, the process exhibits such merits as significantly reduced crystallization duration.

17 Claims, 1 Drawing Sheet

(51) Int. Cl.
  *C01B 39/12* (2006.01)
  *B01J 29/86* (2006.01)
  *B01J 29/89* (2006.01)
  *C01B 39/00* (2006.01)
  *C07C 2/66* (2006.01)

(52) U.S. Cl.
  CPC .............. *C01B 39/12* (2013.01); *C01B 39/48* (2013.01); *C07C 2/66* (2013.01); *C01P 2002/72* (2013.01); *C07C 2529/86* (2013.01)

(56) References Cited

U.S. PATENT DOCUMENTS

| | | |
|---|---|---|
| 3,130,007 A | 4/1964 | Breck |
| 3,702,886 A | 11/1972 | Argauer et al. |
| 4,390,457 A | 6/1983 | Klotz |
| 4,410,501 A | 10/1983 | Taramasso et al. |
| 6,080,382 A | 6/2000 | Lee et al. |
| 2011/0011810 A1 | 1/2011 | Lorgouilloux et al. |
| 2011/0130579 A1 | 6/2011 | Müller et al. |
| 2017/0128918 A1* | 5/2017 | Yang ........................ B01J 29/86 |

OTHER PUBLICATIONS

Paul Wagner et al. Electron diffraction structure solution of a Nanocrystalline Zeolite at Atomic Resolution, J. Phys. Chem. B, Sep. 11, 1999, pp. 8245-8250, 103 (39), 10.121/jp991389j, 1999 American Chemical Society.

European Patent Office, Office Action for EP 16197927.3, dated Jul. 26, 2018.

Korean Patent Office, Office Action for KR 10-2016-0149036, dated Jul. 11, 2018.

* cited by examiner

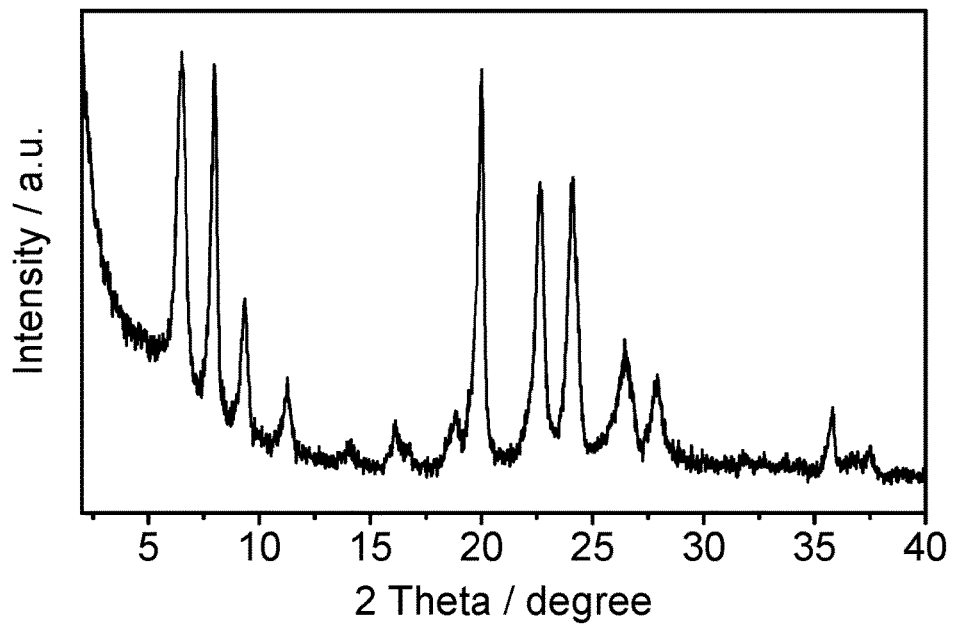

PROCESS FOR PRODUCING A MOLECULAR SIEVE HAVING THE SFE STRUCTURE, MOLECULAR SIEVE HAVING THE SFE STRUCTURE AND USE THEREOF

TECHNICAL FIELD

The present invention relates to a molecular sieve having the SFE structure, a process for producing same and use thereof.

BACKGROUND ART

In industry, porous inorganic materials have been widely used as catalysts and catalyst carriers. These porous materials generally include amorphous porous materials, crystalline molecular sieves and modified layered materials. Minute difference in the structure between any two materials may indicate significant difference in properties like catalytic performance and adsorbing ability therebetween, and further difference in available parameters used to characterize same, such as morphology, specific surface area or pore size.

The structure of a molecular sieve is specifically confirmed by the X-ray diffraction pattern (XRD), while the X-ray diffraction pattern (XRD) is determined by X-ray powder diffraction with a Cu—K α-ray source and a Ni filter. Different molecular sieves have different characterizing XRD patterns. Known molecular sieves, like A-Type Zeolite, Y-Type Zeolite, MCM-22 molecular sieve and so on, have their characterizing XRD patterns respectively.

At the same time, two molecular sieves, if sharing the same characterizing XRD pattern but comprising different combination of skeleton elements, will be identified as different molecular sieves. For example, TS-1 molecular sieve (U.S. Pat. No. 4,410,501) and ZSM-5 molecular sieve (U.S. Pat. No. 3,702,886), share the same characterizing XRD pattern but comprise different combination of skeleton elements. Specifically, TS-1 molecular sieve comprises Si and Ti as the skeleton elements, exhibiting a catalytic oxidation ability, while ZSM-5 molecular sieve comprises Si and Al as the skeleton elements, exhibiting an acidic catalytic ability.

Further, two molecular sieves, if sharing the same characterizing XRD pattern and the same combination of skeleton elements but with different relative amounts of the skeleton elements, will be identified as different molecular sieves as well. For example, Zeolite X (U.S. Pat. No. 2,882,244) and Zeolite Y (U.S. Pat. No. 3,130,007), share the same characterizing XRD pattern and the same combination of skeleton elements (Si and Al), but with different relative amounts of Si and Al. Specifically, Zeolite X has a Si/Al molar ratio of less than 1.5, while Zeolite Y has a Si/Al molar ratio of greater than 1.5.

Among the known molecular sieves, molecular sieves having the SFE structure share the same XRD pattern as illustrated in the following table. The typical molecular sieve having the SFE structure is SSZ-48 molecular sieve (having a chemical composition of 40<$XO_2/Y_2O_3$<100), which was sythensized by the Chevron company on the year of 1997 (U.S. Pat. No. 6,080,382).

| 2θ (°)[a] | d-spacing (Å)[b] | Relative intensity ($I/I_0 \times 100$) |
|---|---|---|
| 6.50 | 13.59 | w-s |
| 7.98 | 11.07 | s-vs |
| 9.36 | 9.45 | m |
| 11.27 | 7.85 | w-m |
| 20.02 | 4.43 | s |
| 22.65 | 3.92 | vs |
| 24.13 | 3.69 | vs |
| 26.45 | 3.37 | w-m |
| 27.92 | 3.19 | w-m |
| 35.95 | 2.50 | m |

[a]±0.3°,
[b]changed with 2θ.

J. Phys. Chem. B 1999, 103, 8245-8250 reported a process for producing the SSZ-48 molecular sieve, wherein $SiO_2/B_2O_3$=63 and the crystallization duration is 49 days. Microporous and Mesoporous Materials 52 (2002) 19-28 reported a process for producing the SSZ-48 molecular sieve, wherein $SiO_2/B_2O_3$=42 and the crystallization duration is 60 days, or $SiO_2/B_2O_3$=50 and a crystallization duration of 42 days.

INVENTION SUMMARY

The present inventors, on the basis of the prior art, found a novel process for producing a molecular sieve having the SFE structure, as compared with the prior art, which exhibits at least such merits as significantly reduced crystallization duration, whereby achieving the present invention. Specifically, this invention relates to the following aspects.

1. A process for producing a molecular sieve having the SFE structure, including a step of crystallizing a mixture comprising a first oxide source, a second oxide source, an organic template and water to obtain a molecular sieve having the SFE structure, and optionally, a step of calcinating the obtained molecular sieve, wherein the organic template is selected from a compound represented by the following formula (A), a quaternary ammonium salt thereof and a quaternary ammonium hydroxide thereof, preferably 4-dimethylamino pyridine,

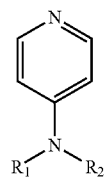

(A)

wherein $R_1$ and $R_2$ may be identical to or different from each other, each independently representing a $C_{1-8}$ alkyl, preferably a $C_{1-4}$ alkyl, more preferably a $C_{1-2}$ alkyl.

2. The process according to anyone of the preceding aspects, wherein the first oxide source is at least one selected from the group consisting of a silicon source and a germanium source, preferably a silicon source, the second oxide source is at least one selected from the group consisting of an aluminum source, a boron source, an iron source, a gallium source, a titanium source, a rare earth source, an indium source and a vanadium source, preferably a boron source or a combination of a boron source and at least one selected from the group consisting of an aluminum source, an iron source, a gallium source, a titanium source, a rare earth source, an indium source and a vanadium source, more preferably a boron source, a combination of a boron source and an aluminum source or a combination of a boron source and a titanium source.

3. The process according to anyone of the preceding aspects, wherein the ratio by molar between the first oxide source (as the first oxide), the second oxide source (as the second oxide), the organic template and water is 1:(0-½): (0.01-2.0):(4-50), preferably 1:(0.001-⅓):(0.01-1.6):(4-40), more preferably 1:(0.002-0.25):(0.01-1.0):(4-40), more preferably 1:(0.004-0.1):(0.01-1.0):(4-30), more preferably 1:(0.004-0.05):(0.01-0.9):(4-30), further preferably 1:(0.004-0.025):(0.01-0.8):(4-30), further preferably 1:(0.005-0.02):(0.02-0.8):(4-30), further preferably 1:(0.01-0.02):(0.04-0.7):(4-26).

4. The process according to anyone of the preceding aspects, wherein the crystallization is conducted under crystallization conditions, and the crystallization conditions include: a crystallization temperature of 130-210 degrees Celsius, preferably 140-190 degrees Celsius, a crystallization duration of 10 hrs to 10 days, preferably 10 hrs to 5 days, more preferably 1-3 days.

5. The process according to anyone of the preceding aspects, wherein the mixture comprises a fluorine source, and the ratio by molar of the fluorine source to the first oxide source (as the first oxide) is (0.1-2.0):1, preferably (0.1-1.0): 1, more preferably (0.1-0.6):1.

6. The process according to anyone of the preceding aspects, wherein the first oxide source and the second oxide source are derived from the same molecular sieve comprising simultaneously the first oxide and the second oxide.

7. The process according to anyone of the preceding aspects, wherein the molecular sieve having the SFE structure has an empirical chemical composition as illustrated by the formula "the first oxide∩the second oxide", wherein the ratio by molar of the first oxide to the second oxide is 2-500, preferably 3-500, more preferably 10-400, more preferably 20-250, more preferably more than 40 less than 250, more preferably 50-200, more preferably 50-100, the first oxide is at least one selected from the group consisting of silica and germanium dioxide, preferably silica, the second oxide is at least one selected from the group consisting of alumina, boron oxide, iron oxide, gallium oxide, titanium oxide, rare earth oxides, indium oxide and vanadium oxide, preferably boron oxide or a combination of boron oxide and at least one selected from the group consisting of alumina, iron oxide, gallium oxide, titanium oxide, rare earth oxides, indium oxide and vanadium oxide, more preferably boron oxide, a combination of boron oxide and alumina or a combination of boron oxide and titanium oxide, the molecular sieve having the SFE structure is preferably an SSZ-48 molecular sieve.

8. A molecular sieve having the SFE structure, having an empirical chemical composition as illustrated by the formula "$SiO_2.Al_2O_3$", an empirical chemical composition as illustrated by the formula "$SiO_2.B_2O_3.Al_2O_3$", or an empirical chemical composition as illustrated by the formula "$SiO_2.B_2O_3.TiO_2$", wherein $SiO_2/Al_2O_3$=1:(0-½), preferably $SiO_2/Al_2O_3$=1:(0.002-0.1), more preferably $SiO_2/Al_2O_3$=1:(0.004-0.05), more preferably $SiO_2/Al_2O_3$=1:(0.004-0.025), more preferably $SiO_2/Al_2O_3$=1:(0.005-0.02), more preferably $SiO_2/Al_2O_3$=1:(0.01-0.02), or, $SiO_2/(B_2O_3+Al_2O_3)$=1:(0-½), preferably $SiO_2/(B_2O_3+Al_2O_3)$=1:(0.002-0.1), more preferably $SiO_2/(B_2O_3+Al_2O_3)$=1:(0.004-0.05), more preferably $SiO_2/(B_2O_3+Al_2O_3)$=1:(0.004-0.025), more preferably $SiO_2/(B_2O_3+Al_2O_3)$=1:(0.005-0.02), more preferably $SiO_2/(B_2O_3+Al_2O_3)$=1:(0.01-0.02), or $SiO_2/(B_2O_3+TiO_2)$=1:(0-½), preferably $SiO_2/(B_2O_3+TiO_2)$=1:(0.002-0.1), more preferably $SiO_2/(B_2O_3+TiO_2)$=1:(0.004-0.05), more preferably $SiO_2/(B_2O_3+TiO_2)$=1:(0.004-0.025), more preferably $SiO_2/(B_2O_3+TiO_2)$=1:(0.005-0.02), more preferably $SiO_2/(B_2O_3+TiO_2)$=1:(0.01-0.02).

9. A molecular sieve composition, comprising a molecular sieve produced in line with the process according to anyone of the preceding aspects or the molecular sieve according to anyone of the preceding aspects, and a binder.

10. Use of a molecular sieve produced in line with the process according to anyone of the preceding aspects, the molecular sieve according to anyone of the preceding aspects or the molecular sieve composition according to anyone of the preceding aspects as an adsorbent or a catalyst for converting an organic compound.

11. Use according to anyone of the preceding aspects, wherein the catalyst for converting an organic compound is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst and an aromatic disproportionation catalyst.

TECHNICAL EFFECTS

According to the present invention, the process for producing a molecular sieve having the SFE structure has been significantly simplified as compared with the prior art, whereby making it easier to produce a molecular sieve having the SFE structure, and therefore is more industrially feasible. According to the present invention, as compared with the prior art, the crystallization duration has been significantly reduced with the present process for producing a molecular sieve having the SFE structure. For example, to produce SSZ-48 molecular sieve, the prior art generally needs a duration of about 42 days, while according to the present invention, the duration is more likely 2 days or even shorter. As the crystallization duration is reduced, it is possible to shorten the production period of a molecular sieve having the SFE structure, leading to energy consumption reduction.

According to the present invention, as compared with the prior art, it is possible to significantly reduce the amount of water to be used with the present process for producing a molecular sieve having the SFE structure. For example, to produce for example SSZ-48 molecular sieve, the ratio by molar of $H_2O$ to the first oxide may be reduced to as low as 5 or less in the process of the present invention. Reduction in the water consumption will lead to great increase in one pot yield, great increase in production efficiency, and at the same time, significant reduction in energy consumption and waste water production.

According to the present invention, as compared with the prior art, it is possible to significantly reduce the amount of the organic template to be used with the present process for producing a molecular sieve having the SFE structure. For example, to produce for example SSZ-48 molecular sieve, the ratio by molar of the organic template to the first oxide may be reduced to as low as 0.05 or less. Reduction in the organic template consumption will lead to great reduction in production cost and nitrogen-containing waste water production, revealing an environmental-friendly nature.

According to the present invention, it is possible for the present process for producing a molecular sieve having the SFE structure to directly (e.g. by one step crystallization) produce a hetero-atom (for example Ti or Al) containing molecular sieve having the SFE structure. By directly producing a hetero-atom containing molecular sieve having the SFE structure, the problems like complicate production procedure, high production cost and insufficient introduction of hetero-atom in associated with the prior art can be effectively solved.

FIGURE DESCRIPTION

FIG. 1 illustrates the X-ray diffraction pattern (XRD) of the molecular sieve produced in Example 1.

SPECIFIC MODE TO CARRY OUT THIS INVENTION

This invention will be described in details hereinafter with reference to the following specific embodiments. However, it should be noted that the protection scope of this invention should not be construed as limited to these specific embodiments, but rather determined by the attached claims.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention.

Further, to the extent that any meaning or definition of a term in this document conflicts with any meaning or definition of the same term in a document incorporated by reference, the meaning or definition assigned to that term in this document shall govern.

In the context of this specification, a molecular sieve, before any other material (for example, organic templates) than water and metal ions that has been filled into its pores during the production thereof is removed from the pores, is referred to as "precursor".

In the context of this specification, in the XRD data of the molecular sieve, w, m, s, vs indicate the intensity of a diffraction peak, with w referring to weak, m to medium, s to strong, vs to very strong, which has been well known in this field. In general, w represents a value of less than 20; m represents a value of 20-40; s represents a value of 40-70; vs represents a value of greater than 70.

In the context of this specification, the molecular sieve structure is confirmed by the X-ray diffraction pattern (XRD), while the X-ray diffraction pattern (XRD) is determined by X-ray powder diffraction with a Cu—K α-ray source and a Ni filter. Before determination, the crystalline state of the test sample is observed under scanning electron microscope (SEM), to confirm that there presents only one type of crystal therein, which indicates that the molecular sieve as the test sample presents as a pure phase, and then the XRD determination is conducted thereon, in order to ensure that there is no interfering peak of other crystal in the XRD pattern. In the context of this specification, by specific surface area, it refers to the total area per unit of mass of a sample, including the internal surface area and the external surface area. A non-porous material has only external surface area, like Portland cement or some clay mineral powder, while a porous material has an external surface area and an internal surface area, like asbestos fiber, diatomite or molecular sieves. In a porous material, the surface area of pores having a diameter of less than 2 nm is referred to as internal surface area, while the surface area obtained by subtracting the internal surface area from the total surface area is referred to as external surface area. The external surface area per unit of mass of a sample is referred to as external specific surface area.

In the context of this specification, by pore volume, it refers to the volume of pores per unit of mass of a porous material (e.g. a molecular sieve). By total pore volume, it refers to the volume of all pores (generally involving only pores having a pore diameter of less than 50 nm) per unit of mass of a molecular sieve. By micropore volume, it refers to the volume of all micropores (generally referred to pores having a pore diameter of less than 2 nm) per unit of mass of a molecular sieve.

The present invention relates to a process for producing a molecular sieve having the SFE structure. As the molecular sieve having the SFE structure, it is preferably SSZ-48 molecular sieve. In view of this, according to a preferred embodiment of the present invention, this invention relates to a process for producing an SSZ-48 molecular sieve.

According to the present invention, the molecular sieve having the SFE structure has an empirical chemical composition as illustrated by the formula "the first oxide∩the second oxide". It is known that, a molecular sieve will sometimes (especially immediately after the production thereof) contain a certain amount of water, however, this invention does not specify or identify as to how much this amount may be, since the presence or absence of water will not substantially change the XRD pattern of the present molecular sieve. In this context, the empirical chemical composition actually represents an anhydrous chemical composition of this molecular sieve.

Further, it is obvious that the empirical chemical composition represents the framework chemical composition of the molecular sieve.

According to the present invention, in the molecular sieve, the ratio by molar of the first oxide to the second oxide is generally 2-500, preferably 3-500, more preferably 10-400, more preferably 20-250, more preferably more than 40 less than 250, more preferably 50-200, more preferably 50-100.

According to the present invention, in the molecular sieve, the first oxide is at least one selected from the group consisting of silica and germanium dioxide, preferably silica.

According to the present invention, in the molecular sieve, the second oxide is at least one selected from the group consisting of alumina, boron oxide, iron oxide, gallium oxide, titanium oxide, rare earth oxides, indium oxide and vanadium oxide, preferably boron oxide or a combination of boron oxide and at least one selected from the group consisting of alumina, iron oxide, gallium oxide, titanium oxide, rare earth oxides, indium oxide and vanadium oxide, more preferably boron oxide, a combination of boron oxide and alumina or a combination of boron oxide and titanium oxide.

According to one embodiment of the present invention, the first oxide is silica, and the second oxide is boron oxide.

According to another embodiment of the present invention, the first oxide is at least one selected from the group consisting of silica and germanium dioxide, and the second oxide is boron oxide. According to another embodiment of the present invention, the first oxide is silica, and the second oxide is at least one selected from the group consisting of boron oxide and alumina.

According to one embodiment of the present invention, if multiple oxides are used in combination, the ratio by molar between each two oxides is generally 1-99.6:99-0.4, preferably 33-99.5:67-0.5, more preferably 50-99:50-1, more preferably 60-99:40-1, more preferably 66-98:34-2, more preferably 66-97:34-3.

According to one embodiment of the present invention, the molecular sieve having the SFE structure has an empirical chemical composition as illustrated by the formula "$SiO_2.B_2O_3$", wherein $SiO_2/B_2O_3=1:(0-½)$, preferably $SiO_2/B_2O_3=1:(0.002-0.1)$, more preferably $SiO_2/B_2O_3=1:(0.004-0.05)$, more preferably $SiO_2/B_2O_3=1:(0.004-0.025)$, more preferably $SiO_2/B_2O_3=1:(0.005-0.02)$, more preferably $SiO_2/B_2O_3=1:(0.01-0.02)$.

According to one embodiment of the present invention, the molecular sieve having the SFE structure has an empirical chemical composition as illustrated by the formula "$SiO_2.Al_2O_3$", wherein $SiO_2/Al_2O_3=1:(0-½)$, preferably $SiO_2/Al_2O_3=1:(0.002-0.1)$, more preferably $SiO_2/Al_2O_3=1:(0.004-0.025)$, more preferably $SiO_2/Al_2O_3=1:(0.004-0.05)$, more preferably $SiO_2/Al_2O_3=1:(0.005-0.02)$, more preferably $SiO_2/Al_2O_3=1:(0.01-0.02)$.

According to one embodiment of the present invention, the molecular sieve having the SFE structure has an empirical chemical composition as illustrated by the formula "$SiO_2.B_2O_3.Al_2O_3$", wherein $SiO_2/(B_2O_3+Al_2O_3)=1:(0-½)$, preferably $SiO_2/(B_2O_3+Al_2O_3)=1:(0.002-0.1)$, more preferably $SiO_2/(B_2O_3+Al_2O_3)=1:(0.004-0.05)$, more preferably $SiO_2/(B_2O_3+Al_2O_3)=1:(0.004-0.025)$, more preferably $SiO_2/(B_2O_3+Al_2O_3)=1:(0.005-0.02)$, more preferably $SiO_2/(B_2O_3+Al_2O_3)=1:(0.01-0.02)$.

According to one embodiment of the present invention, the molecular sieve having the SFE structure has an empirical chemical composition as illustrated by the formula "$SiO_2.B_2O_3.TiO_2$", wherein $SiO_2/(B_2O_3+TiO_2)=1:(0-½)$, preferably $SiO_2/(B_2O_3+TiO_2)=1:(0.002-0.1)$, more preferably $SiO_2/(B_2O_3+TiO_2)=1:(0.004-0.05)$, more preferably $SiO_2/(B_2O_3+TiO_2)=1:(0.004-0.025)$, more preferably $SiO_2/(B_2O_3+TiO_2)=1:(0.005-0.02)$, more preferably $SiO_2/(B_2O_3+TiO_2)=1:(0.01-0.02)$.

According to the present invention, the molecular sieve has a specific surface area (by the BET method) of 250-600 $m^2/g$, preferably 280-450 $m^2/g$.

According to the present invention, the molecular sieve has a micropore volume (by the t-plot method) of 0.05-0.25 $cm^3/g$, preferably 0.08-0.18 $cm^3/g$.

According to the present invention, the molecular sieve has a pore size (by the Argon adsorption method) of 0.6-0.73 nm, preferably 0.62-0.68 nm.

According to the present invention, the molecular sieve in the calcined form has X ray diffraction pattern as substantially illustrated in the following table, whereby indicating an SFE structure.

| 2θ (°)[a] | d-spacing (Å)[b] | Relative intensity ($I/I_0 \times 100$) |
|---|---|---|
| 6.50 | 13.59 | w-s |
| 7.98 | 11.07 | s-vs |
| 9.36 | 9.45 | m |
| 11.27 | 7.85 | w-m |
| 20.02 | 4.43 | s |
| 22.65 | 3.92 | vs |
| 24.13 | 3.69 | vs |
| 26.45 | 3.37 | w-m |
| 27.92 | 3.19 | w-m |
| 35.95 | 2.50 | m |

[a]±0.3°,
[b]changed with 2θ.

According to the present invention, the process for producing the molecular sieve includes a step of crystallizating a mixture comprising a first oxide source, a second oxide source, an organic template and water (hereinafter referred to as the mixture) under crystallization conditions, to obtain a molecular sieve having the SFE structure (hereinafter referred to as the crystallization step).

According to a preferred embodiment of the present invention, the crystallization is conducted in one single step, i.e. presenting as one step crystallization. By the one step crystallization of the present invention, it is possible to directly obtain a molecular sieve having the SFE structure with the mixture, especially a molecular sieve having the SFE structure containing a hetero atom (for example Ti or Al).

As compared with the multiple step crystallization of the prior art, this represents a technological breakthrough. For example, according to this preferred embodiment of the present invention, by crystallizating a mixture comprising simultaneously a silicon source, a boron source, an aluminum source, an organic template and water under crystallization conditions, it is possible to directly obtain a molecular sieve having the SFE structure as illustrated by the formula.

"$SiO_2.B_2O_3.Al_2O_3$". However, according to the prior art (involving multiple step crystallization), it is only possible to obtain a molecular sieve having the SFE structure as illustrated by the formula "$SiO_2.B_2O_3.Al_2O_3$" by firstly obtaining a molecular sieve having the SFE structure as illustrated by the formula "$SiO_2.B_2O_3$" and then introducing Al into the structure of the molecular sieve. According to the present invention, in the process for producing the molecular sieve, the organic template may be a compound represented by the following formula (A), a quaternary ammonium salt thereof or a quaternary ammonium hydroxide thereof, preferably 4-dimethylamino pyridine.

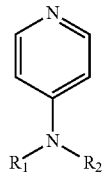

(A)

According to the present invention, in the formula (A), $R_1$ and $R_2$ may be identical to or different from each other, each independently representing a $C_{1-8}$ alkyl, preferably a $C_{1-4}$ alkyl, more preferably a $C_{1-2}$ alkyl, most preferably both methyl.

According to the present invention, as the quaternary ammonium salt of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, there may be exemplified a halo ion like $Br^-$, but not limiting thereto.

According to the present invention, as the quaternary ammonium hydroxide of the compound represented by the formula (A), there may be exemplified a quaternary nitrogen ($N^+$) structure obtained by additionally bonding a $C_{1-8}$ alkyl (preferably a $C_{1-4}$ alkyl, more preferably a $C_{1-2}$ alkyl or methyl) to the N atom in addition to the groups $R_1$ and $R_2$. As the counterion of the quaternary nitrogen, a hydroxyl ion ($OH^-$) is needed.

According to the present invention, in the process for producing the molecular sieve, the crystallization step can be conducted in line with any way known in this field, there may be exemplified a way of mixing the first oxide source, the second oxide source, the organic template and water in predetermined ratios, and then hydrothermally crystallizating the obtained mixture under crystallization conditions.

According to the present invention, in the process for producing the molecular sieve, the crystallization conditions include: a crystallization temperature of 130-210 degrees Celsius, preferably 140-190 degrees Celsius, a crystallization duration of 10 hrs to 10 days, preferably 10 hrs to 5 days, more preferably 1-3 days.

According to the present invention, in the process for producing the molecular sieve, the first oxide source is at least one selected from the group consisting of a silicon source and a germanium source, preferably a silicon source.

According to the present invention, in the process for producing the molecular sieve, the second oxide source is at least one selected from the group consisting of an aluminum source, a boron source, an iron source, a gallium source, a titanium source, a rare earth source, an indium source and a vanadium source, preferably a boron source or a combination of a boron source and at least one selected from the group consisting of an aluminum source, an iron source, a gallium source, a titanium source, a rare earth source, an indium source and a vanadium source, more preferably a boron source, a combination of a boron source and an aluminum source or a combination of a boron source and a titanium source.

According to one embodiment of the present invention, in the process for producing the molecular sieve, the first oxide source is at least one selected from the group consisting of silicic acid, silica gel, silica sol, tetralkoxysilane, water glass and germanium dioxide, the second oxide source is at least one selected from the group consisting of boric acid, boron oxide, sodium metaborate, aluminum hydroxide, sodium aluminate, aluminum salts, aluminum alkoxides, kaolin, montmorillonite, tetra-n-butyl titanate and titanium tetrachloride.

According to one embodiment of the present invention, in the process for producing the molecular sieve, the first oxide source is at least one selected from the group consisting of silicic acid, silica gel, silica sol, tetralkoxysilane, water glass and germanium dioxide, the second oxide source is a combination of at least one selected from the group consisting of boric acid, boron oxide and sodium metaborate and at least one selected from the group consisting of aluminum hydroxide, sodium aluminate, aluminum salts, kaolin, montmorillonite, tetra-n-butyl titanate, and titanium tetrachloride. As the aluminum salts, there may be exemplified aluminum sulfate, aluminum nitrate, aluminum carbonate, aluminum phosphate, aluminum chloride or alum. As the aluminum alkoxides, there may be exemplified aluminum isopropoxide, aluminum ethoxide, aluminum butoxide.

According to the present invention, in the process for producing the molecular sieve, as the first oxide source, any corresponding oxide source known in this field for this purpose can be used. For example, if the first oxide is silica, as the first oxide source (silicon source), there may be exemplified silicic acid, silica gel, silica sol, tetralkoxysilane or water glass. If the first oxide is germanium dioxide, as the first oxide source (germanium source), there may be exemplified tetralkoxy germanium, germanium dioxide, germanium nitrate. As the first oxide source, one kind or a mixture of two or more kinds at any ratio therebetween could be used.

According to the present invention, in the process for producing the molecular sieve, as the second oxide source, any corresponding oxide source known in this field for this purpose can be used, including but not limiting to the oxides, alkoxides, oxometallates, acetates, oxalates, ammonium salts, sulfates and nitrates of the corresponding metal in the second oxide. For example, if the second oxide is alumina, as the second oxide source (aluminum source), there may be exemplified aluminum hydroxide, sodium aluminate, aluminum salts, aluminum alkoxides, kaolin or montmorillonite. As aluminum salts, there may be exemplified aluminum sulfate, aluminum nitrate, aluminum carbonate, aluminum phosphate, aluminum chloride or alum. As aluminum alkoxides, there may be exemplified aluminum isopropoxide, aluminum ethoxide, aluminum butoxide. If the second oxide is boron oxide, as the second oxide source (boron source), there may be exemplified boric acid, borate salt, borax, diboron trioxide. If the second oxide is iron oxide, as the second oxide source (iron source), there may be exemplified ferric nitrate, ferric chloride, iron oxide. If the second oxide is gallium oxide, as the second oxide source (gallium source), there may be exemplified gallium nitrate, gallium sulfate, gallium oxide. If the second oxide is titanium oxide, as the second oxide source (titanium source), there may be exemplified titanium tetralkoxide, titania, titanium nitrate. If the second oxide is rare earth oxides, as the second oxide source (rare earth source), there may be exemplified lanthanum oxide, neodymium oxide, yttrium oxide, cerium oxide, lanthanum nitrate, neodymium nitrate, yttrium nitrate, ceric ammonium sulfate. If the second oxide is indium oxide, as the second oxide source (indium source), there may be exemplified indium chloride, indium nitrate, indium oxide. If the second oxide is vanadium oxide, as the second oxide source (vanadium source), there may be exemplified vanadium chloride, ammonium metavanadate, sodium vanadate, vanadium dioxide, vanadyl sulfate. As the second oxide source, one kind or a mixture of two or more kinds at any ratio therebetween could be used.

According to one embodiment of the present invention, for the first oxide source, if multiple oxide sources are used in combination, the ratio by molar between each two oxide sources is generally 1-99.6:99-0.4, preferably 33-99.5:67-0.5, more preferably 50-99:50-1, more preferably 60-99:40-1, more preferably 66-98:34-2, more preferably 66-97:34-3.

According to one embodiment of the present invention, for the second oxide source, if multiple oxide sources are used in combination, the ratio by molar between each two oxide sources is generally 1-99.6:99-0.4, preferably 33-99.5:67-0.5, more preferably 50-99:50-1, more preferably 60-99:40-1, more preferably 66-98:34-2, more preferably 66-97:34-3.

According to one embodiment of the present invention, in the process for producing the molecular sieve, the first oxide source and the second oxide source may be derived from the same source, specifically there may be exemplified a molecular sieve comprising simultaneously the first oxide and the second oxide. Herein, as the molecular sieve, there may be exemplified ERB-1 molecular sieve, Ti-MWW molecular sieve, Y molecular sieve, Beta molecular sieve, ZSM-5 molecular sieve, B-ZSM-5 molecular sieve, Fe-ZSM-5 molecular sieve, B-MWW molecular sieve or TS-1 molecular sieve.

According to one embodiment of the present invention, in the process for producing the molecular sieve, the ratio by molar between the first oxide source (as the first oxide), the second oxide source (as the second oxide), the organic template and water is 1:(0-½):(0.01-2.0):(4-50), preferably 1:(0.001-⅓):(0.01-1.6):(4-40), more preferably 1:(0.002-0.25):(0.01-1.0):(4-40), more preferably 1:(0.004-0.1):

(0.01-1.0):(4-30), more preferably 1:(0.004-0.05):(0.01-0.9):(4-30), further preferably 1:(0.004-0.025):(0.01-0.8):(4-30), further preferably 1:(0.005-0.02):(0.02-0.8):(4-30), further preferably 1:(0.01-0.02):(0.04-0.7):(4-26).

According to one embodiment of the present invention, in the process for producing the molecular sieve, from the point of facilitating obtaining the molecular sieve of the present invention, the mixture does not contain an alkaline source. As the alkaline source, there may be exemplified alkaline substances excepting the first oxide source, the second oxide source and the organic template, specifically there may be exemplified any alkaline source conventionally used in this field for alkalizing the reaction system, more specifically there may be exemplified inorganic alkali containing alkali metal or alkaline earth metal as the cation, especially NaOH and KOH. Herein, by "does not contain an alkaline source", it means not intentionally or on purpose introducing into the mixture an alkaline source.

According to one embodiment of the present invention, in the process for producing the molecular sieve, from the point of facilitating obtaining the molecular sieve of the present invention, the mixture may further comprise a fluorine source, or may not comprise a fluorine source. As the fluorine source, there may be exemplified fluoride or an aqueous solution thereof, especially HF. Herein, the ratio by molar of the fluorine source (if any) to the first oxide source (as the first oxide) is (0.1-2.0):1, preferably (0.1-1.0):1, more preferably (0.1-0.6):1. According to one embodiment of the present invention, in the process for producing the molecular sieve, from the point of facilitating obtaining the molecular sieve of the present invention, at least at the beginning of the crystallization step, preferably throughout the crystallization step, the mixture is controlled at pH=6-14, preferably pH=7-14, more preferably 8-14, more preferably 8.5-13.5, more preferably 9-12, more preferably 9-11.

According to this invention, in the process, upon completion of the crystallization step, any separation method conventionally known in this field may be used to isolate a molecular sieve from the obtained reaction mixture as the final product, whereby obtaining the molecular sieve of the present invention. As the separation method, there may be exemplified a method wherein the obtained reaction mixture is filtered, washed and dried. Herein, filtering, washing and drying can be conducted in any manner conventionally known in this field. Specifically, as the filtration, there may be exemplified a method of simply suction filtering the obtained reaction mixture. As the washing, there may be exemplified a method of washing with deionized water. As the drying temperature, there may be exemplified a temperature of 40-250 degrees Celsius, preferably a temperature of 60-150 degrees Celsius, as the drying duration, there may be exemplified a duration of 8-30 h, preferably a duration of 10-20 h. The drying could be conducted under the normal pressure or a reduced pressure.

According to this invention, in the process, if needed, the obtained molecular sieve could be calcinated so as to remove the organic template and any water therefrom, whereby obtaining a calcinated molecular sieve (i.e. the molecular sieve in the calcined form), which corresponds to the molecular sieve of the present invention as well. The calcination could be conducted in any manner conventionally known in this field, for example, the calcination temperature is generally 300-800 degrees Celsius, preferably 400-650 degrees Celsius, while the calcination duration is generally 1-10 h, preferably 3-6 h. Further, the calcination is generally conducted under an oxygen containing atmosphere, for example, under the air atmosphere or under oxygen atmosphere According to the present invention, the obtained molecular sieves may be used in any physical form, for example, powder, particulate or a molded product (for example, strip, clover). These physical forms can be obtained in any manner conventionally known in this field, without any specific limitation thereto.

The molecular sieve according to this invention may be combined with other material, whereby obtaining a molecular sieve composition. As these other materials, there may be exemplified an active material and a non-active material. As the active material, there may be exemplified synthesized zeolites and natural zeolites, as the non-active material (generally referred to as binder), there may be exemplified clay, white earth, silica gel and alumina. As these other materials, one kind or a mixture of two or more kinds at any ratio therebetween could be used. As the amount of these other materials, any amount conventional used in this field could be used, without any specific limitation thereto.

The molecular sieve or the molecular sieve composition of the present invention can be used as an adsorbent, for example, that to be used in a gaseous or liquid phase to isolate at least one component from a mixture made of multiple components. In this way, a part of or substantially all of the at least one component can be isolated from the mixture. Specifically there may be exemplified a way wherein the molecular sieve or the molecular sieve composition is made to contact the mixture, whereby selectively adsorbing this component.

The molecular sieve or the molecular sieve composition of the present invention may be directly or after treated or converted (for example after ion exchanged) in a way conventionally used in this field regarding a molecular sieve used as a catalyst for converting an organic compound (or as a catalytic active component thereof). Specifically, according to the present invention, for example, reactants can be made to conduct a predetermined reaction in the presence of the catalyst for converting an organic compound to obtain the aimed product. As the predetermined reaction, there may be exemplified isomerization of normal paraffins, liquid phase alkylation between benzene and ethylene to produce ethyl benzene, liquid phase alkylation between benzene and propene to produce iso-propyl benzene, butene isomerization, naphtha cracking reaction, alkylation of benzene with ethanol, cyclohexenen hydration, toluene disproportionation to produce p-xylene, alkylation of toluene with methanol to produce p-xylene or disproportionation of iso-propyl naphthalene to produce 2,6-di(iso-propyl) naphthalene. In view of this, as the catalyst for converting an organic compound, there may be exemplified an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst or an aromatic disproportionation catalyst.

EXAMPLE

The following examples illustrate rather than limit this invention.

Example 1

10.995 g of the organic template 4-dimethylamino pyridine, 54.0 g water, 0.470 g boric acid, 22.5 g silica sol (containing $SiO_2$ 40 wt %) were mixed till homogeneous, to obtain a mixture with a ratio (ratio by molar) of:

$SiO_2/B_2O_3=40$ 4-dimethylamino pyridine/$SiO_2$=0.6

$H_2O/SiO_2=25$ and then charged into a stainless steel reactor, under stirring at 175 degrees Celsius crystallized for 3 days, upon completion of the crystallization, filtered, washed, dried to obtain a molecular sieve precursor, which was then at 650 degrees Celsius in air calcined for 6 hours to obtain a molecular sieve.

The XRD data of the resultant molecular sieve were listed in Table 1, while the XRD pattern thereof was as illustrated in FIG. 1.

The resultant molecular sieve has a specific surface area of 331 m²/g, a micropore volume of 0.12 cm³/g.

If determined by inductively coupled plasma-atomic emission spectroscopy (ICP), the sample after calcined has $SiO_2/B_2O_3=45.5$.

TABLE 1

| 2θ/° | d/Å | I/I₀ × 100 |
|---|---|---|
| 6.555 | 13.472 | 36.2 |
| 8.053 | 10.9694 | 85 |
| 9.376 | 9.4243 | 29.9 |
| 11.35 | 7.7899 | 10 |
| 14.145 | 6.2559 | 7.4 |
| 16.278 | 5.4409 | 14.5 |
| 16.831 | 5.2633 | 13.6 |
| 18.624 | 4.7604 | 16.3 |
| 18.956 | 4.6778 | 13.1 |
| 20.221 | 4.3879 | 65 |
| 22.825 | 3.8928 | 81.2 |
| 24.225 | 3.6709 | 100 |
| 26.749 | 3.33 | 20.4 |
| 28.146 | 3.1678 | 20.1 |
| 32.118 | 2.7846 | 3.2 |
| 32.683 | 2.7377 | 3.7 |
| 33.976 | 2.6364 | 2.8 |
| 36.156 | 2.4823 | 24.8 |
| 37.71 | 2.3835 | 3.7 |

Example 2

36.651 g of the organic template 4-dimethylamino pyridine, 45 g water, 3.488 g germanium dioxide, 1.336 g boric acid 75 g silica sol (containing $SiO_2$ 40 wt %) were mixed till homogeneous, to obtain a mixture with a ratio (ratio by molar) of:

$(SiO_2+GeO_2)/B_2O_3=50$ 4-dimethylamino pyridine/$SiO_2$=0.6

$H_2O/SiO_2=10$ and then, charged into a stainless steel reactor, under stirring at 180 degrees Celsius crystallized for 2 days, upon completion of the crystallization, filtered, washed, dried, to obtain a molecular sieve in the synthesized form.

The XRD data of the resultant molecular sieve were listed in Table 2 while the XRD pattern is similar to FIG. 1.

The resultant molecular sieve has a specific surface area of 346 m²/g, a micropore volume of 0.12 cm³/g.

If determined by inductively coupled plasma-atomic emission spectroscopy (ICP), the sample after calcined has $SiO_2/GeO_2=18.3$, $SiO_2/B_2O_3=52.5$.

TABLE 2

| 2θ/° | d/Å | I/I₀ × 100 |
|---|---|---|
| 6.517 | 13.5515 | 19.2 |
| 7.993 | 11.0521 | 71.8 |
| 9.336 | 9.465 | 21.7 |
| 11.331 | 7.8028 | 23.7 |
| 14.13 | 6.2626 | 6.7 |
| 16.218 | 5.4609 | 12.2 |
| 16.671 | 5.3134 | 12.4 |
| 18.506 | 4.7904 | 14.4 |
| 18.801 | 4.716 | 10.7 |
| 20.123 | 4.4091 | 60.8 |
| 22.765 | 3.9029 | 71.7 |
| 24.146 | 3.6828 | 100 |
| 26.473 | 3.3641 | 23.4 |
| 27.952 | 3.1894 | 20 |
| 29.25 | 3.0507 | 2.9 |
| 31.955 | 2.7984 | 3.2 |
| 32.668 | 2.7389 | 5.1 |
| 33.057 | 2.7076 | 3.7 |
| 34.678 | 2.5846 | 4 |
| 36.038 | 2.4901 | 26.2 |
| 36.924 | 2.4324 | 4.2 |
| 37.517 | 2.3953 | 4.3 |
| 39.017 | 2.3066 | 3.2 |

Example 3

109.95 g of the organic template 4-dimethylamino pyridine, 540 g water, 3.131 g boric acid, 1.313 g aluminum hydroxide, 225.0 g silica sol (containing $SiO_2$ 40 wt %) were mixed till homogeneous, to obtain a mixture with a ratio (ratio by molar) of:

$SiO_2/(B_2O_3+Al_2O_3)=45$ 4-dimethylamino pyridine/$SiO_2$=0.6

$H_2O/SiO_2=25$ and then, charged into a stainless steel reactor, under stirring at 170 degrees Celsius crystallized for 3 days, upon completion of the crystallization, filtered, washed, dried, and then the precursor was at 650 degrees Celsius in air calcined for 6 hours to obtain a molecular sieve.

The XRD data of the resultant molecular sieve were listed in Table 3 while the XRD pattern is similar to FIG. 1.

The resultant molecular sieve has a specific surface area of 321 m²/g, a micropore volume of 0.13 cm³/g.

If determined by inductively coupled plasma-atomic emission spectroscopy (ICP), the sample after calcined has $SiO_2/B_2O_3=35.2$, $SiO_2/Al_2O_3=88.0$.

TABLE 3

| 2θ/° | d/Å | I/I₀ × 100 |
|---|---|---|
| 6.612 | 13.3574 | 39.2 |
| 8.034 | 10.9964 | 95.6 |
| 9.395 | 9.4055 | 31.6 |
| 11.329 | 7.8042 | 10.7 |
| 14.145 | 6.2561 | 8.4 |
| 16.201 | 5.4666 | 15.9 |
| 16.73 | 5.2947 | 15.9 |
| 18.882 | 4.696 | 11.7 |
| 20.182 | 4.3964 | 63.4 |
| 22.805 | 3.8963 | 74.4 |
| 24.186 | 3.6768 | 100 |
| 26.453 | 3.3666 | 25.4 |
| 28.011 | 3.1828 | 20.5 |
| 31.936 | 2.8 | 2.9 |
| 32.961 | 2.7152 | 4 |
| 34.496 | 2.5978 | 3.1 |

TABLE 3-continued

| 2θ/° | d/Å | I/I₀ × 100 |
|---|---|---|
| 36.058 | 2.4888 | 20.8 |
| 37.729 | 2.3823 | 5.2 |

Example 4

Similar to Example 2, except that $(SiO_2+GeO_2)/B_2O_3=40$, 4-dimethylamino pyridine/$SiO_2=0.8$, $H_2O/SiO_2=25$, at 170 degrees Celsius crystallized for 70 hours.

The XRD data of the resultant molecular sieve were listed in Table 4 while the XRD pattern is similar to FIG. 1

The resultant molecular sieve has a specific surface area of 297 m²/g, a micropore volume of 0.11 cm³/g.

If determined by inductively coupled plasma-atomic emission spectroscopy (ICP), the sample after calcined has $SiO_2/GeO_2=19.2$, $(SiO_2+GeO_2)/B_2O_3=44.2$.

TABLE 4

| 2θ/° | d/Å | I/I₀ × 100 |
|---|---|---|
| 6.575 | 13.4316 | 21.3 |
| 8.034 | 10.9958 | 79.5 |
| 9.377 | 9.4242 | 25.5 |
| 11.425 | 7.7385 | 28.7 |
| 13.387 | 6.6087 | 3 |
| 14.148 | 6.2549 | 6.8 |
| 16.24 | 5.4536 | 12.8 |
| 16.75 | 5.2885 | 14.8 |
| 18.546 | 4.7802 | 14.2 |
| 18.921 | 4.6864 | 11.4 |
| 20.22 | 4.388 | 63.2 |
| 21.533 | 4.1233 | 2.4 |
| 22.844 | 3.8896 | 74.9 |
| 24.225 | 3.6709 | 100 |
| 26.572 | 3.3518 | 23.9 |
| 28.07 | 3.1762 | 21 |
| 29.271 | 3.0486 | 3.5 |
| 32.012 | 2.7935 | 2.7 |
| 33.02 | 2.7105 | 4.1 |
| 34.516 | 2.5964 | 4.7 |
| 36.136 | 2.4836 | 25.7 |
| 36.95 | 2.4308 | 2.9 |
| 37.637 | 2.3879 | 5 |
| 39.155 | 2.2988 | 3.3 |

Example 5

Similar to Example 1, except that $SiO_2/B_2O_3=39$, 4-dimethylamino pyridine/$SiO_2=0.3$, $H_2O/SiO_2=25$, at 170 degrees Celsius crystallized for 3 days.

The XRD data of the resultant molecular sieve were listed in Table 5 while the XRD pattern is similar to FIG. 1.

The resultant molecular sieve has a specific surface area of 343 m²/g, a micropore volume of 0.13 cm³/g.

If determined by inductively coupled plasma-atomic emission spectroscopy (ICP), the sample after calcined has $SiO_2/B_2O_3=41.5$.

TABLE 5

| 2θ/° | d/Å | I/I₀ × 100 |
|---|---|---|
| 6.575 | 13.4314 | 32.8 |
| 8.053 | 10.9703 | 81.4 |
| 9.452 | 9.3493 | 29.7 |
| 11.309 | 7.818 | 10.8 |
| 14.167 | 6.2465 | 8.8 |
| 16.277 | 5.4412 | 12.4 |
| 16.751 | 5.2882 | 15.4 |
| 18.587 | 4.7698 | 16.4 |
| 18.919 | 4.6869 | 12.7 |
| 20.203 | 4.3917 | 64.1 |
| 22.864 | 3.8863 | 84.4 |
| 24.226 | 3.6708 | 100 |
| 26.711 | 3.3347 | 22.1 |
| 28.072 | 3.176 | 24.5 |
| 29.409 | 3.0346 | 4 |
| 32.08 | 2.7878 | 2.3 |
| 33.018 | 2.7107 | 3.4 |
| 34.541 | 2.5945 | 3.3 |
| 36.154 | 2.4824 | 25.3 |
| 37.072 | 2.423 | 2.3 |
| 37.715 | 2.3831 | 4 |

Example 6

Similar to Example 1, except that $SiO_2/B_2O_3=200$, 4-dimethylamino pyridine/$SiO_2=0.2$, $H_2O/SiO_2=30$, at 170 degrees Celsius crystallized for 80 hours.

The XRD data of the resultant molecular sieve were listed in Table 6 while the XRD pattern is similar to FIG. 1.

The resultant molecular sieve has a specific surface area of 347 m²/g, a micropore volume of 0.12 cm³/g.

If determined by inductively coupled plasma-atomic emission spectroscopy (ICP), the sample after calcined has $SiO_2/B_2O_3=168.0$.

TABLE 6

| 2θ/° | d/Å | I/I₀ × 100 |
|---|---|---|
| 6.556 | 13.4705 | 31.5 |
| 8.053 | 10.9705 | 69.9 |
| 9.377 | 9.4239 | 24.2 |
| 11.366 | 7.7789 | 10.3 |
| 14.224 | 6.2214 | 8.2 |
| 16.296 | 5.4349 | 12.9 |
| 16.809 | 5.27 | 14.7 |
| 18.568 | 4.7747 | 15.9 |
| 18.94 | 4.6818 | 13.3 |
| 20.222 | 4.3878 | 63.1 |
| 22.864 | 3.8863 | 83.3 |
| 24.245 | 3.668 | 100 |
| 26.672 | 3.3395 | 24.6 |
| 28.05 | 3.1784 | 21.6 |
| 29.47 | 3.0284 | 3.6 |
| 31.208 | 2.8637 | 1.9 |
| 32.132 | 2.7834 | 3.6 |
| 32.887 | 2.7212 | 3.7 |
| 33.941 | 2.639 | 2.6 |
| 34.674 | 2.5849 | 2.5 |
| 36.155 | 2.4824 | 26.8 |
| 36.855 | 2.4368 | 2.3 |
| 37.677 | 2.3855 | 4.2 |
| 39.184 | 2.2971 | 2.1 |

Example 7

Similar to Example 1, except that $SiO_2/B_2O_3=50$, 4-dimethylamino pyridine/$SiO_2=0.4$, $H_2O/SiO_2=17.5$, at 170 degrees Celsius crystallized for 2 days.

The XRD data of the resultant molecular sieve were listed in Table 7 while the XRD pattern is similar to FIG. 1.

The resultant molecular sieve has a specific surface area of 357 m²/g, a micropore volume of 0.13 cm³/g.

If determined by inductively coupled plasma-atomic emission spectroscopy (ICP), the sample after calcined has $SiO_2/B_2O_3=54.2$.

TABLE 7

| 2θ/° | d/Å | $I/I_0 \times 100$ |
|---|---|---|
| 6.595 | 13.3912 | 30.4 |
| 8.054 | 10.9683 | 80.6 |
| 9.416 | 9.3843 | 26.7 |
| 11.347 | 7.7917 | 9.4 |
| 14.169 | 6.2453 | 7.9 |
| 16.3 | 5.4336 | 13.8 |
| 16.79 | 5.2761 | 11.9 |
| 18.605 | 4.7651 | 15.6 |
| 18.923 | 4.6858 | 13.5 |
| 20.223 | 4.3875 | 63.6 |
| 22.865 | 3.8861 | 82.1 |
| 24.264 | 3.6651 | 100 |
| 26.75 | 3.3299 | 22.5 |
| 28.091 | 3.1739 | 20.4 |
| 29.356 | 3.0399 | 3.5 |
| 32.095 | 2.7865 | 4.2 |
| 32.924 | 2.7182 | 3.7 |
| 34.6 | 2.5903 | 2.5 |
| 36.174 | 2.4811 | 26.3 |
| 36.967 | 2.4297 | 2.5 |
| 37.754 | 2.3808 | 4.6 |

Example 8

Similar to Example 1, except that $SiO_2/B_2O_3=70$, 4-dimethylamino pyridine/$SiO_2=0.5$, $H_2O/SiO_2=25$, at 170 degrees Celsius crystallized for 50 hours.

The XRD data of the resultant molecular sieve were listed in Table 8 while the XRD pattern is similar to FIG. 1.

The resultant molecular sieve has a specific surface area of 342 m²/g, a micropore volume of 0.12 cm³/g.

If determined by inductively coupled plasma-atomic emission spectroscopy (ICP), the sample after calcined has $SiO_2/B_2O_3=69.1$.

TABLE 8

| 2θ/° | d/Å | $I/I_0 \times 100$ |
|---|---|---|
| 6.594 | 13.3928 | 42.3 |
| 8.053 | 10.9692 | 90.8 |
| 9.415 | 9.386 | 32.5 |
| 11.366 | 7.7787 | 12.1 |
| 14.168 | 6.2461 | 10.4 |
| 16.258 | 5.4473 | 13.3 |
| 16.75 | 5.2884 | 16.8 |
| 18.567 | 4.7748 | 18 |
| 18.901 | 4.6912 | 14.6 |
| 20.203 | 4.3917 | 67.1 |
| 22.845 | 3.8895 | 83 |
| 24.263 | 3.6652 | 100 |
| 26.691 | 3.3371 | 25.3 |
| 28.032 | 3.1805 | 25.1 |
| 29.256 | 3.0501 | 3.1 |
| 32.919 | 2.7186 | 4.3 |
| 33.933 | 2.6396 | 2.7 |
| 34.494 | 2.598 | 3.2 |
| 36.136 | 2.4836 | 24 |
| 36.914 | 2.433 | 3.5 |
| 37.715 | 2.3832 | 4.7 |

Example 9

Similar to Example 1, except that $SiO_2/B_2O_3=45$, 4-dimethylamino pyridine/$SiO_2=0.36$, $H_2O/SiO_2=25$, at 170 degrees Celsius crystallized for 2 days.

The XRD data of the resultant molecular sieve were listed in Table 9 while the XRD pattern is similar to FIG. 1.

The resultant molecular sieve has a specific surface area of 331 m²/g, a micropore volume of 0.12 cm³/g.

If determined by inductively coupled plasma-atomic emission spectroscopy (ICP), the sample after calcined has $SiO_2/B_2O_3=49.5$.

TABLE 9

| 2θ/° | d/Å | $I/I_0 \times 100$ |
|---|---|---|
| 6.556 | 13.4713 | 41 |
| 8.055 | 10.9668 | 88.3 |
| 9.415 | 9.3855 | 27.7 |
| 11.366 | 7.7787 | 9.7 |
| 14.169 | 6.2457 | 9.4 |
| 16.335 | 5.4221 | 14.9 |
| 16.752 | 5.2879 | 15.4 |
| 18.566 | 4.775 | 16.1 |
| 18.915 | 4.6877 | 11.8 |
| 20.222 | 4.3877 | 62.3 |
| 22.845 | 3.8895 | 78.1 |
| 24.245 | 3.6679 | 100 |
| 26.612 | 3.3468 | 25.5 |
| 28.05 | 3.1784 | 21.5 |
| 29.414 | 3.0341 | 4 |
| 32.092 | 2.7868 | 2.9 |
| 32.847 | 2.7244 | 3.6 |
| 34.49 | 2.5983 | 3.1 |
| 36.155 | 2.4824 | 23.6 |
| 37.657 | 2.3867 | 4.7 |

Example 10

Similar to Example 3, except that aluminum sulfate was use as the aluminum source, $SiO_2/(Al_2O_3+B_2O_3)=40$, 4-dimethylamino pyridine/$SiO_2=0.4$, $H_2O/SiO_2=25$, at 170 degrees Celsius crystallized for 3 days.

The XRD data of the resultant molecular sieve were listed in Table 10 while the XRD pattern is similar to FIG. 1.

The resultant molecular sieve has a specific surface area of 288 m²/g, a micropore volume of 0.09 cm³/g.

If determined by inductively coupled plasma-atomic emission spectroscopy (ICP), the sample after calcined has $SiO_2/B_2O_3=65.2$, $SiO_2/Al_2O_3=108.3$.

TABLE 10

| 2θ/° | d/Å | $I/I_0 \times 100$ |
|---|---|---|
| 6.478 | 13.6332 | 29.6 |
| 7.995 | 11.0488 | 100 |
| 9.375 | 9.4258 | 31.8 |
| 11.268 | 7.8459 | 9 |
| 14.147 | 6.2551 | 8.4 |
| 16.238 | 5.4542 | 13.1 |
| 16.714 | 5.2997 | 14.1 |
| 18.268 | 4.8524 | 20.8 |
| 18.858 | 4.7018 | 12.3 |
| 20.123 | 4.4091 | 64.3 |
| 22.746 | 3.9063 | 76 |
| 24.166 | 3.6798 | 99.9 |
| 26.414 | 3.3714 | 25.4 |
| 27.913 | 3.1937 | 19.7 |
| 31.974 | 2.7968 | 4.3 |
| 32.665 | 2.7392 | 3.5 |
| 34.328 | 2.6101 | 3.3 |
| 36.074 | 2.4877 | 23.5 |
| 37.573 | 2.3918 | 5.1 |

Example 11

Similar to Example 3, except that aluminum nitrate was used as the aluminum source, $SiO_2/(Al_2O_3+B_2O_3)=100$, 4-dimethylamino pyridine/$SiO_2$=0.3, $H_2O/SiO_2$=25, at 170 degrees Celsius crystallized for 3 days.

The XRD data of the resultant molecular sieve were listed in Table 11 while the XRD pattern is similar to FIG. 1.

The resultant molecular sieve has a specific surface area of 288 m$^2$/g, a micropore volume of 0.09 cm$^3$/g.

If determined by inductively coupled plasma-atomic emission spectroscopy (ICP), the sample after calcined has $SiO_2/B_2O_3$=95.2, $SiO_2/Al_2O_3$=266.3.

TABLE 11

| 2θ/° | d/Å | I/I$_0$ × 100 |
|---|---|---|
| 6.515 | 13.5549 | 39.1 |
| 8.016 | 11.021 | 98.7 |
| 9.357 | 9.4436 | 29.2 |
| 11.269 | 7.8457 | 10.1 |
| 14.072 | 6.2884 | 9.9 |
| 16.278 | 5.4408 | 16.5 |
| 16.73 | 5.2949 | 14.7 |
| 18.605 | 4.7652 | 17.1 |
| 20.163 | 4.4003 | 66.9 |
| 22.786 | 3.8994 | 77.8 |
| 24.224 | 3.6711 | 100 |
| 26.493 | 3.3616 | 25.1 |
| 28.03 | 3.1807 | 20.2 |
| 32.056 | 2.7898 | 3.1 |
| 32.7 | 2.7363 | 4.3 |
| 36.078 | 2.4875 | 22.4 |
| 37.678 | 2.3854 | 4.4 |

Example 12

Similar to Example 1, except that HF was introduced as the fluorine source, $SiO_2/B_2O_3$=45, 4-dimethylamino pyridine/$SiO_2$=0.5, F/$SiO_2$=0.4, $H_2O/SiO_2$=25, at 170 degrees Celsius crystallized for 48 hours.

The XRD data of the resultant molecular sieve were listed in Table 12 while the XRD pattern is similar to FIG. 1.

The resultant molecular sieve has a specific surface area of 318 m$^2$/g, a micropore volume of 0.10 cm$^3$/g.

If determined by inductively coupled plasma-atomic emission spectroscopy (ICP), the sample after calcined has $SiO_2/B_2O_3$=51.2.

TABLE 12

| 2θ/° | d/Å | I/I$_0$ × 100 |
|---|---|---|
| 6.595 | 13.3909 | 30.3 |
| 8.053 | 10.9699 | 100 |
| 9.432 | 9.3693 | 39.2 |
| 11.31 | 7.817 | 12.4 |
| 14.166 | 6.2466 | 8.7 |
| 16.258 | 5.4473 | 12.8 |
| 16.729 | 5.2952 | 14.2 |
| 18.528 | 4.7848 | 15.8 |
| 18.883 | 4.6958 | 12.9 |
| 20.145 | 4.4042 | 31.4 |
| 22.784 | 3.8997 | 48.1 |
| 24.168 | 3.6795 | 55.9 |
| 26.629 | 3.3448 | 20.4 |
| 27.971 | 3.1872 | 20.6 |
| 28.507 | 3.1285 | 4.8 |
| 29.154 | 3.0606 | 4.3 |
| 32.028 | 2.7922 | 1.5 |
| 32.783 | 2.7295 | 3.7 |
| 34.42 | 2.6034 | 3.4 |
| 36.057 | 2.4889 | 10.8 |
| 37.598 | 2.3903 | 4.2 |
| 38.997 | 2.3077 | 1.6 |

Example 13

Similar to Example 1, except that tetra-n-butyl titanate was added as the titanium source, $SiO_2/B_2O_3$=40, $SiO_2/TiO_2$=50, 4-dimethylamino pyridine/$SiO_2$=0.8, $H_2O/SiO_2$=25, at 170 degrees Celsius crystallized for 3 days.

The XRD data of the resultant molecular sieve were listed in Table 13 while the XRD pattern is similar to FIG. 1.

The resultant molecular sieve has a specific surface area of 335 m$^2$/g, a micropore volume of 0.10 cm$^3$/g.

If determined by inductively coupled plasma-atomic emission spectroscopy (ICP), the sample after calcined has $SiO_2/B_2O_3$=46.2, $SiO_2/TiO_2$=55.1.

TABLE 13

| 2θ/° | d/Å | I/I$_0$ × 100 |
|---|---|---|
| 6.457 | 13.6776 | 34.2 |
| 7.993 | 11.0518 | 95 |
| 9.337 | 9.4641 | 27.1 |
| 11.29 | 7.8307 | 8.2 |
| 14.104 | 6.274 | 7 |
| 16.199 | 5.4672 | 14.5 |
| 16.632 | 5.3259 | 13.6 |
| 18.526 | 4.7853 | 14.9 |
| 20.122 | 4.4093 | 58.9 |
| 22.668 | 3.9195 | 71.9 |
| 24.088 | 3.6915 | 100 |
| 26.396 | 3.3738 | 23.1 |
| 27.991 | 3.185 | 20.4 |
| 31.951 | 2.7987 | 3.1 |
| 32.594 | 2.745 | 4.8 |
| 35.959 | 2.4954 | 24.3 |
| 37.495 | 2.3966 | 5.7 |

Example 14

Similar to Example 1, except that $SiO_2/B_2O_3$=40, 4-dimethylamino pyridine/$SiO_2$=0.06, $H_2O/SiO_2$=5, at 170 degrees Celsius crystallized for 3 days, upon completion of the crystallization, filtered, washed, dried to obtain a molecular sieve precursor, and then the precursor was at 650 degrees Celsius in air calcined for 6 hours to obtain a molecular sieve.

The XRD data of the resultant molecular sieve were listed in Table 14 while the XRD pattern is similar to FIG. 1.

The resultant molecular sieve has a specific surface area of 292 m$^2$/g, a micropore volume of 0.10 cm$^3$/g.

If determined by inductively coupled plasma-atomic emission spectroscopy (ICP), the sample after calcined has $SiO_2/B_2O_3$=46.8.

TABLE 14

| 2θ/° | d/Å | I/I$_0$ × 100 |
|---|---|---|
| 6.558 | 13.4677 | 24.6 |
| 8.056 | 10.9655 | 77 |
| 9.4 | 9.4012 | 25.2 |
| 11.311 | 7.8162 | 8.1 |
| 14.231 | 6.2184 | 5.8 |

TABLE 14-continued

| 2θ/° | d/Å | I/I₀ × 100 |
|---|---|---|
| 16.854 | 5.2562 | 10.1 |
| 18.828 | 4.7094 | 9.7 |
| 20.228 | 4.3863 | 61 |
| 22.892 | 3.8816 | 71 |
| 24.253 | 3.6668 | 100 |
| 26.678 | 3.3387 | 19.5 |
| 28.099 | 3.173 | 17.2 |
| 29.342 | 3.0414 | 2.7 |
| 32.132 | 2.7834 | 3.5 |
| 32.878 | 2.7219 | 3.1 |
| 33.822 | 2.648 | 2.4 |
| 36.187 | 2.4802 | 26.8 |
| 37.111 | 2.4205 | 2.2 |
| 37.803 | 2.3778 | 4.5 |
| 46.821 | 1.9387 | 5.1 |

Example 15

30 g of the molecular sieve produced in Example 3 in the form of powder was ion-exchanged by an aqueous ammonium nitrate solution (with a concentration of 1 mol/L) for 4 times, filtered, and dried at 110 degrees Celsius, calcined at 500 degrees Celsius in air for 6 hours. Then, 1.5 g of the calcined molecular sieve was charged into a 100 ml stainless steel reactor, further introducing therein 35 g iso-propyl naphthalene, and closed the reactor. At 250° C., under 200 rpm stirring, the reaction was conducted for 48 hours. Upon completion of the reaction, the system was cooled to the room temperature, after centrifugally isolating the molecular sieve powder therefrom, the reaction product was analysed on an Agilent 19091N-236 gas chromatograph, indicating an iso-propyl naphthalene conversion of 22.82%, and a total selectivity to the aimed product 2,6-di(iso-propyl) naphthalene and 2,7-di(iso-propyl) naphthalene of 79.88%.

We claim:

1. A process for producing a molecular sieve, comprising:
preparing a mixture comprising a first oxide source, a second oxide source, an organic template, and water;
crystallizing the mixture to obtain a molecular sieve having a SFE structure; and
optionally calcinating the obtained molecular sieve,
wherein the organic template is selected from a compound represented by formula (A), a quaternary ammonium salt thereof, and a quaternary ammonium hydroxide thereof,

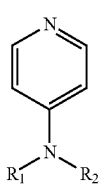

(A)

wherein $R_1$ and $R_2$ are identical to or different from each other, each independently representing a $C_{1-2}$ alkyl,
wherein the first oxide source is at least one selected from the group consisting of a silicon source and a germanium source,
wherein the second oxide source is a boron source or a combination of the boron source and at least one compound selected from the group consisting of an aluminum source, an iron source, a gallium source, a titanium source, a rare earth source, an indium source, and a vanadium source,
wherein a molar ratio of the first oxide source (as the first oxide), the second oxide source (as the second oxide), the organic template, and water is 1:(0.002-0.25):(0.01-1.0):(4-40), and
wherein the crystallizing step is conducted at a crystallization temperature of 130-210 degrees Celsius for a crystallization duration of 1-3 days.

2. The process according to claim 1, wherein the first oxide source is a silicon source, the second oxide source is at least one selected from the group consisting of the boron source, the combination of the boron source and the aluminum source, and the combination of the boron source and the titanium source.

3. The process according to claim 1, wherein the molar ratio of the first oxide source (as the first oxide), the second oxide source (as the second oxide), the organic template, and water is 1:(0.004-0.05):(0.01-0.9):(4-30).

4. The process according to claim 1, wherein the crystallization temperature is 140-190 degrees Celsius.

5. The process according to claim 1, wherein the mixture further comprises a fluorine source, and a molar ratio of the fluorine source to the first oxide source (as the first oxide) is (0.1-2.0):1.

6. The process according to claim 1, wherein the first oxide source and the second oxide source are derived from a same molecular sieve comprising the first oxide and the second oxide.

7. The process according to claim 1, wherein the molecular sieve has an empirical chemical composition represented by the formula "the first oxide∩the second oxide", wherein a molar ratio of the first oxide to the second oxide is 3-500, the first oxide is at least one selected from the group consisting of silica and germanium dioxide, the second oxide is boron oxide or a combination of boron oxide and at least one selected from the group consisting of alumina, iron oxide, gallium oxide, titanium oxide, rare earth oxides, indium oxide, and vanadium oxide, and the molecular sieve is an SSZ-48 molecular sieve.

8. The process according to claim 7, wherein the molar ratio of the first oxide to the second oxide is 10-400, the first oxide is silica, the second oxide is at least one selected from the group consisting of boron oxide, a combination of boron oxide and alumina, and a combination of boron oxide and titanium oxide.

9. A method of converting an organic compound, comprising contacting the organic compound with a catalyst comprising a molecular sieve produced with the process according to claim 1.

10. The method of claim 9, wherein the catalyst is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, and an aromatic disproportionation catalyst.

11. A method for separating a component from a mixture, comprising contacting the mixture with an adsorbent comprising the molecular sieve produced with the process according to claim 1.

12. A molecular sieve having a SFE structure, having an empirical chemical composition represented by formula "$SiO_2.Al_2O_3$", wherein $SiO_2/Al_2O_3$=1:(0.002-0.1), formula "$SiO_2.B_2O_3.Al_2O_3$", wherein $SiO_2/(B_2O_3+Al_2O_3)$=1:(0.002-0.1), or formula "$SiO_2.B_2O_3.TiO_2$", wherein $SiO_2/$ $(B_2O_3+TiO_2)=1:(0.002-0.1)$, and wherein, in a calcined form, having a X ray diffraction pattern as substantially illustrated in the following table:

| 2θ (°) [a] | d-spacing (Å) [b] | Relative intensity (I/I₀ × 100) |
|---|---|---|
| 6.50 | 13.59 | w-s |
| 7.98 | 11.07 | s-vs |
| 9.36 | 9.45 | M |
| 11.27 | 7.85 | w-m |
| 20.02 | 4.43 | S |
| 22.65 | 3.92 | Vs |
| 24.13 | 3.69 | Vs |
| 26.45 | 3.37 | w-m |
| 27.92 | 3.19 | w-m |
| 35.95 | 2.50 | M | wherein a means±0.3°, b means changed with 2θ, w represents a value of less than 20, m represents a value of 20-40, s represents a value of 40-70, vs represents a value of greater than 70.

13. A molecular sieve composition, comprising the molecular sieve according to claim 12 and a binder.

14. A method of converting an organic compound, comprising contacting the organic compound with a catalyst comprising the molecular sieve according to claim 12.

15. The method of claim 14, wherein the catalyst is at least one selected from the group consisting of an alkane isomerization catalyst, a catalyst for the alkylation between olefins and aromatics, an olefin isomerization catalyst, a naphtha cracking catalyst, a catalyst for the alkylation between alcohols and aromatics, an olefin hydration catalyst, and an aromatic disproportionation catalyst.

16. A method for separating a component from a mixture, comprising contacting the mixture with an adsorbent comprising the molecular sieve of claim 12.

17. A method for separating a component from a mixture, comprising contacting the mixture with an adsorbent comprising the molecular sieve composition according to claim 12.

* * * * *